US 6,514,526 B1

(12) United States Patent
Forssell et al.

(10) Patent No.: US 6,514,526 B1
(45) Date of Patent: Feb. 4, 2003

(54) COATED STARCH CAPSULES AND A PROCESS FOR PRODUCING THEM

(75) Inventors: Pirkko Forssell, Helsinki (FI); Päivi Myllärinen, Helsinki (FI); Jyrki Heinämäki, Helsinki (FI); Päivi Palviainen, Kerava (FI); Jouko Yliruusi, Vantaa (FI); Kaisa Poutanen, Helsinki (FI)

(73) Assignee: Valtion teknillinen tutkimuskeskus, VTT (FI)

( * ) Notice: Subject to any disclaimer, the term of this patent is extended or adjusted under 35 U.S.C. 154(b) by 0 days.

(21) Appl. No.: 09/647,157

(22) PCT Filed: Mar. 29, 1999

(86) PCT No.: PCT/FI99/00260

§ 371 (c)(1),
(2), (4) Date: Sep. 27, 2000

(87) PCT Pub. No.: WO99/52512

PCT Pub. Date: Oct. 21, 1999

(30) Foreign Application Priority Data

Mar. 27, 1998 (FI) .................................................. 980707
Mar. 27, 1998 (FI) .................................................. 980708

(51) Int. Cl.[7] .................................................. A61K 9/48
(52) U.S. Cl. ........................ 424/463; 424/400; 424/443; 424/451; 424/456; 424/489; 424/490; 424/502
(58) Field of Search ................................ 424/400, 443, 424/451, 456, 463, 489, 490, 502

(56) References Cited

U.S. PATENT DOCUMENTS

| 4,859,377 A | 8/1989 | Shasha et al. |
| 5,160,745 A | 11/1992 | DeLuca et al. |
| 5,726,161 A | 3/1998 | Whistler |

FOREIGN PATENT DOCUMENTS

WO    A1-9734645    9/1997

*Primary Examiner*—Thurman K. Page
*Assistant Examiner*—Charesse Evans
(74) *Attorney, Agent, or Firm*—Birch, Stewart, Kolasch & Birch, LLP

(57) ABSTRACT

The invention relates to starch capsules which protect various substances, such as peptides, proteins, particularly pharmaceutical peptides and proteins, drugs or flavouring agents or spices or enzymes against the effect of the environment or the intestines. Filled starch granules are coated with a suitable biopolymer such as starch or amylose.

34 Claims, 3 Drawing Sheets

COATED STARCH CAPSULES AND A PROCESS FOR PRODUCING THEM

Figure 1:
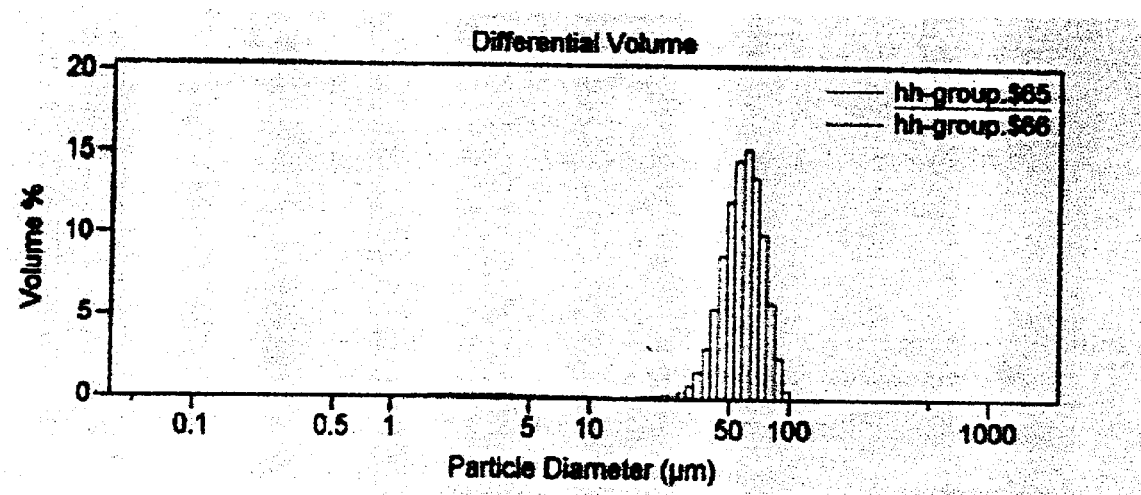

This application is the national phase under 35 U.S.C. §371 of PCT International Application No. PCT/FI99/00260 which has an International filing date of Mar. 29, 1999, which designated the United States of America.

The present invention relates to starch capsules. More precisely, the invention relates to coated starch capsules and the manufacture of such capsules.

In oral medical treatment, it is often justifiable to direct the release of a drug at the area of the intestines on a spot-specific basis. Many drugs do not tolerate well the acidic conditions of the stomach or they irritate the mucous membranes of the stomach (even to the effect of causing corrosion of a different degree in long-term use). The intention is to direct such drugs in a controlled way to the small intestine or the large intestine where they are absorbed and/or take effect locally in the most efficient way. Oral dosing of new drugs with peptide and protein structures is also used with the intention to release drugs on the spot-specific basis (pharmaceutical peptides are acid-labile and are not absorbed until the large intestine). It has been predicted that the use of pharmaceutical peptides and proteins will increase, which has aroused the interest of pharmaceutical industry, among others, in spot-specific pharmaceutical preparations.

Traditionally, spot-specific pharmaceutical preparations (so-called entero preparations) are prepared in multiple stages by a film coating technique in which solid nuclei containing drugs—granules, pellets or tablets—are enveloped in a pH-sensitive polymeric capsule. The manufacture involves some multivariable processes that are difficult to control. According to present knowledge, entero preparations should rather be formulated into multiple-unit preparations, for example, into film-coated granules or pellets which are encased in a capsule coat. The migration of the small entero granules and pellets in the alimentary tract, which are released from the multiple-unit preparations, is not dependent on the food consumed or on the speed of emptying the stomach.

The transfer of drugs in the intestines should be possible all the way to the large intestine and, on the other hand, it should be possible to store them at room temperature. Several drugs on the market are sensitive to fluctuations in ambient conditions during storage (for example, humidity, light, oxygen, and temperature). During storage, the drug may decompose chemically (chemical impurities), leading to impaired quality and efficacy of the phrmaceutical product. During storage, the physical and pharmaceutical properties of the drug formulation can also deteriorate. As regards solid drug formulations, for example, the package rarely gives sufficient protection to a labile drug and drug formulation, but other manufacturing methods should be used to guarantee the quality of the pharmaceutical preparation.

The purpose of the present invention is to provide a certain type of protective capsule which can be used to protect drugs against ambient impact so that the quality and the efficacy of the drugs will not change before they reach their destination. The purpose of the protective capsule is to protect the drugs against physical and chemical decomposition so that the drugs keep at room temperature for rather long periods of time. Another purpose of the protective capsule is to give protection against the acidity of the stomach and bile acids as well as other conditions in the intestines so that the quality and the efficacy of the drugs keep in the intestines as long as is appropriate from the viewpoint of the medicine's effect.

The present invention is based on the surprising observation that capsules can be formed from starch granules which give the drugs exactly the desired protection.

International patent publication WO 89/04842 describes the use of starch granules as a carrier for absorbed functional compositions. The starch granules are treated with alpha-amylase or glucoamylase. The publication suggests that starch granules be used as adjuvants for antiperspirants or as bulking agents for foods and drinks. It suggests that liquid substances be formulated, by using treated starch granules, into a powder, paste or cream formulation which is easier to pack or otherwise more practical. To strengthen the structure of hydrolyzed starch granules, the publication suggests treatment of the starch with cross-linking agents, such as sodium trimetaphosphate. If the substance to be absorbed into the starch granules has a lipid character, the starch matrix can, according to the publication, be treated with substances that render the pore surfaces more lipophilic. Such substances include, for example, synthetic polymers such as methylcellulose. The publication mentions that the substances to be absorbed can be, for example, salad oils, flavours, insect repellents, insecticides, herbicides, perfumes, moisturizers, soaps, waxes, body creams and lotions, vitamins and therapeutic drugs.

U.S. Pat. No. 5,670,490 describes porous aggregates formed of starch granules with the aid of binding agents, the empty space inside the aggregates being used to carry various functional substances. The substances are released from the aggregate under the influence of mechanical compression/decomposition, by disintegration of the binding agents or other substances, or by dissolution or diffusion from the porous surface. The diameter of the round aggregates was 15–150 $\mu$m. Typically, the binding agent was a polymer. The patent suggests the use of aggregates in formulating orally dosed pharmaceutical compounds, among others, so that the formulation protects the active ingredients against the acidic and decomposing conditions of the stomach and that the active ingredients would not be released until the small intestine. The aggregates were prepared by suspending the starch granules in a suitable solution containing binding agents and by spray drying the suspension. According to the publication, the aggregates could be coated with a polymer after putting the functional compounds inside the aggregates. The binding agents could be biodegradable polymers, such as polysaccharides (gums originating from algae or plants, pectins, agar-agar, alginate, gelatine, dextrin, starch derivatives) and cellulose-bearing substances, such as carboxy-methyl cellulose, hydroxy-methyl cellulose, hydroxy-propyl cellulose, etc., proteins, particularly those which are not inherently present in starch granules, as well as polyesters. The polymers could also be non-biodegradable, synthetic or semi-synthetic, such as polyvinyl alcohol poly-N-vinyl-2-pyrrolidone or polymers or copolymers of acrylic or methacrylic acid or their amide derivatives, such as polyacrylamide. The coating substances could be the same or different polymers than the binding agents. The functional substances that could be absorbed into the aggregates could be the same substances as listed in application WO 89/04842.

U.S. Pat. No. 4,551,177 describes a compressible starch that can be used as a binder for tablets. Cold-water-insoluble granular starch was treated with acid, alkali or alpha-amylase, whereby altered, weakened granules were obtained which, when compressed, showed a good binding capacity.

Patent publication EP 0 539 910 A1 describes the treatment of starch granules with an amylase. The intention was to modify the viscosity of the starch granules. The publication suggests that the amylase-treated starch granules be used in instant liquid food, for example, or as mixed with non-treated starch granules, whereby blends of starch granules having various viscosity values can be obtained. According to the publication, the amylase-treated starch granules adsorb hydrophobic substances such as aromatic compounds. The publication states that glucoamylase-treated starch granules are able to adsorb oils.

The publication of Milosevic et al., Journal of Controlled Release 38 (1996) 75–84, describes the use of amylose films to protect pharmaceutical preparations. According to the publication, insoluble polymers, such as ethyl cellulose, were used to control the swelling and decomposition of the amylose and, thus, the releasing speed of the drug in conditions that simulated the conditions of the alimentary tract. According to the publication, the release of the drug from the preparation was due to the decomposition of the amylose component of the compound under the effect of bacterial enzymes and not because of mechanical decomposition of the coating.

Prior art publications, such as the publications WO 89/04842 and U.S. Pat. No. 5,670,490 referred to above, suggest that various functional substances be protected by using starch granules. In the formation of aggregates described in U.S. Pat. No. 5,670,490, various binding agents are used, for example, various polymers which can be detrimental when taken into the organs or during the manufacturing process. One disadvantage of the method disclosed in patent publication WO 89/04842 is that hydrolyzed starch granules can, indeed, absorb various substances inside their porous structures, but the substances can be released out of the starch granules and, on the other hand, the substances are not protected against the impact of the environment (light, pH, humidity, oxygen, temperature).

The purpose of the present invention is to eliminate the disadvantages of the prior art technology and to provide a whole new protective method for drugs and pharmaceutical peptides and proteins which advantageously employs natural polymers. By using the method, various substances, other than drugs as well, can be protected against the effects of the environment during storage or in human or animal intestines.

The method according to the invention utilizes the porous structure of starch granules, as a consequence of which the desired substances can be attached to the surface of the starch granules or the starch granules can be filled with these substances. The surface of a granule is coated with a thin layer of a biopolymer that is capable of film forming, such as cellulose, pectin, protein, preferably starch. The starch surface can be formulated from starch dissolved in hot water or from a component of the starch, an amylose, or by closing the pores on the surface of the starch granule by smaller starch granules of a suitable size. In the method according to the invention, aggregates are not formed from the starch granules but the granules remain essentially separate.

The porosity of the starch granules can further be improved by hydrolyzing to change the structure thereof so that the surface has holes and the inside is porous, cavitary, whereby the internal space of the granule forms a hollow, capsule-type space. The capsule-type space of the hydrolyzed starch granules can be filled with desired substances. The larger the molecule size of the drug or other substance, the more advantageous it is that the starch granule be hydrolyzed because compounds having large molecules can be better accommodated into the cavities of the hydrolyzed starch granules.

The present invention is based on the fact that non-hydrolyzed or hydrolyzed starch granules filled with the desired substances are coated with natural biopolymers, preferably with starch. The starch, one of its component, a linear amylose in particular, is capable of film forming. The starch can be modified by physical means (for example, by means of temperature) so that it becomes more stable and more resistant against the liquids of the stomach and the small intestine. The various techniques for coating starch granules include spraying with a starch/amylose solution or mixing the granules with a starch/amylose solution and allowing the starch to crystallize onto the surface of the granule. The starch/amylose solution can also be precipitated onto the surface of the granules by using ethanol. According to one embodiment of the invention, the pores on the surface of the granule can be closed with suitably small starch granules. Instead of the starch/amylose, the coating of starch granules can be carried out by employing other biopolymers, if their film forming properties and dissolving properties are as good as those of the amylose starch. Such biopolymers include, for example, cellulose, pectin or protein.

According to an advantageous embodiment of the invention, the starch granules are hydrolyzed by using enzymes. The starch is hydrolyzed with amylolytic enzymes, such as alpha-amylases, β-amylases, and glucoamylases. The amorphic components of the granule are hydrolyzed and the crystalline areas remain. These crystalline components are fairly stable also in the human alimentary tract. After hydrolyzation, the starch granule can be filled with the desired substances, such as drugs, pharmaceutical peptides or proteins. The ability of the starch capsules to preserve various hydrophilic and hydrophobic substances can be used, for example, to improve the stability of volatile drugs and flavouring agents.

The starch capsules are preferably prepared from natural starch. Starches of various origins deviate as to their size and composition. These differences can be utilized in different applications.

One object of the invention is starch capsules, which comprise starch granules which have a porous structure and are coated with biopolymer. Before coating, the starch capsules can be filled with desired substances.

Another object of the invention is a method for manufacturing the starch capsules, comprising the following stages:
  selecting starch granules of a suitable size in accordance with the purpose of use,
  coating the selected starch granules with a biopolymer. Before coating, the starch capsules can be filled with desired substances.

The porosity of the starch granules is preferably increased by hydrolyzing the starch granule so that its structure becomes more cavitary. The cavitary structure of the granules can accommodate more substances which the granules are to protect.

With the aid of the invention, considerable advantages can be obtained. The starch granules according to the invention keep well at room temperature for several months. Starch capsules according to the invention, containing drugs, can be kept at room temperature for long periods of time. The quality and the efficacy of the drug improve when the drug is not exposed to the effect of fluctuations in humidity, temperature, oxygen or acidity in its environment.

The efficacy of pharmaceutical substances encased in the starch capsules according to the invention improves when the release of the drug takes place at the desired spot in the small or the large intestine. On the basis of the invention, the planning of the oral dosage of whole new pharmaceutical substances can be started.

The durability of various substances added to foodstuffs, such as flavouring agents and spices, encased in the starch capsules according to the invention, and the release thereof when eating is improved. For example, the taste of sweets such as chewing gum keeps longer when the release of the flavouring agents encased in the starch granule takes place in a controlled way.

The durability of various enzymes can also be improved by attaching them to the surface of the starch granules or into their porous internal spaces, and by preferably coating them with a biopolymer. Examples of such enzymes include industrial enzymes, such as those used by the wood-processing, the textile, and the food industry, the activity and the efficacy of which should not essentially be reduced during preservation, storage and/or processing. For example, it is advantageous to protect baking enzymes with the capsules according to the invention because baking enzymes should keep active until they are used in baking. It is also advantageous to use capsules according to the invention to protect the enzymes used in the same way as drugs, such as the enzyme that decomposes lactose, because they should withstand preservation and storage, as well as the intestinal conditions.

In the following, the present invention is studied more closely with the aid of a detailed description and exemplary embodiments.

FIG. 1. The size distribution of separated starch granules on Coulter.

Figure 2:

FIG. 2. A starch granule hydrolyzed by an alpha-amylase.

Figure 3:
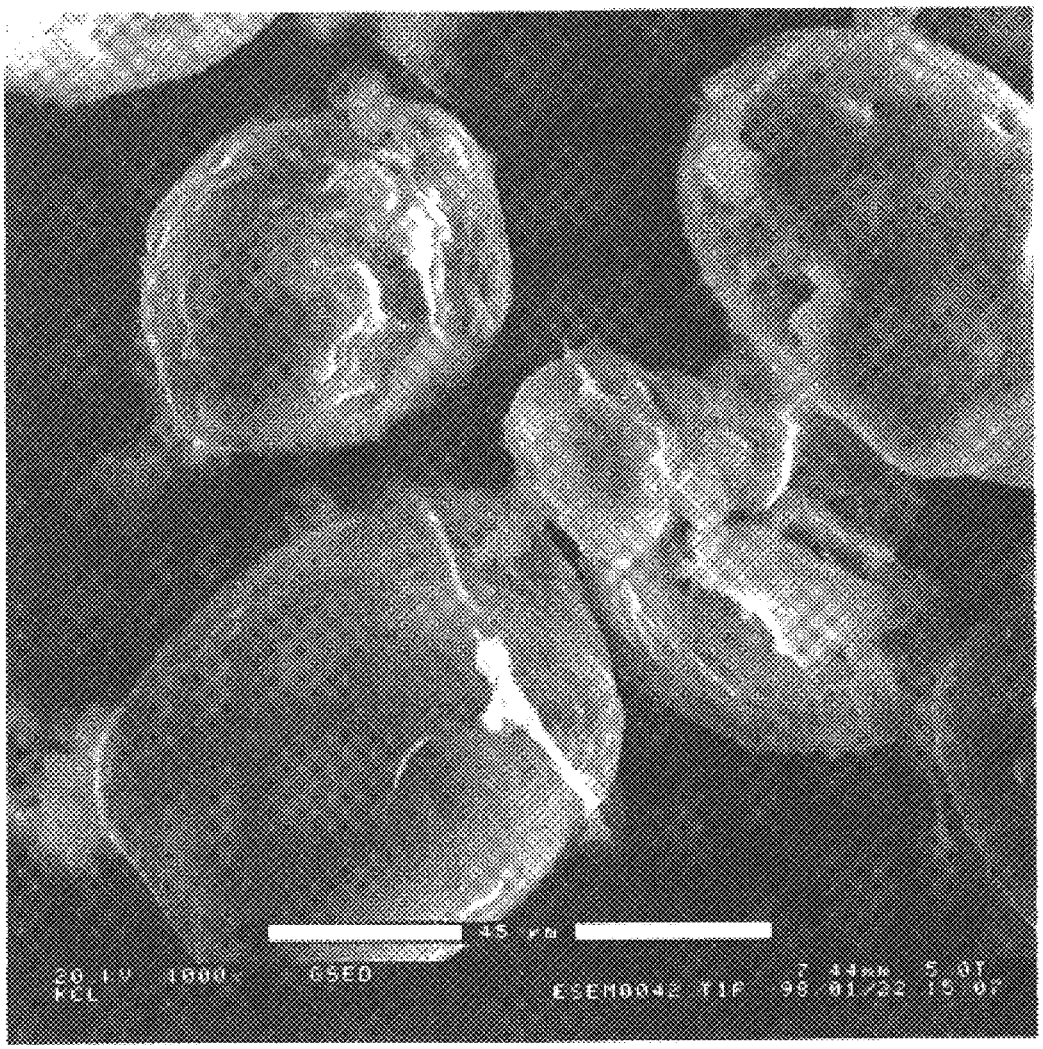

FIG. 3. A starch granule coated with amylose.

Starch is the reserve polysaccharide of plants. It consists of two polymers of glucose, the linear amylose and the amylopectin that is very branched. The starch granules can be hydrolyzed with amylolytic enzymes, such as alpha-amylases. In that case, the amorphic components of the starch granules are hydrolyzed and the crystalline areas remain. Starches of various origins deviate as to their size and composition.

The starch used in manufacturing the starch capsules is preferably natural starch. It can originate from barley, potato, wheat, oats, pea, corn, tapioca, sago, rice or similar tuber vegetable or corn crop, it preferably originates from potato, barley, wheat or corn.

Starch granules of a suitable size can be separated from the starch by suspending the starch in water, by mixing and allowing the starch granules to sediment. The solution and small granules are poured out of the top of the sediment. The sedimentation can be repeated several times (2 to 10 times) and the granules thus obtained can be freeze-dried.

The present invention employs starch granules having a size of 10 to 100 $\mu$m, preferably 30 to 100 $\mu$m, most preferably 50 to 100 $\mu$m. When starch granules are prepared which are hydrolyzed and filled with, for example, drugs or proteins having large molecules, it is preferable to choose large starch granules. When hydrolyzing, larger cavities are formed in larger granules, whereby more substances having large molecules can be accommodated in the cavities. Should the starch granules be used to protect substances having small molecules, the starch granules need not necessarily be hydrolyzed and, in that case, it can be more advantageous to use small starch granules, 10 to 50 $\mu$m. The pores or holes inherently present in starch granules are about 10 nm or smaller. When starch granules are hydrolyzed, the size of the holes becomes 1 to 10 $\mu$m. Holes made by alpha-amylase, for example, are about 1 $\mu$m. The molecular size of the substance to be filled dictates which size starch granules are suitable and whether hydrolyzing is needed, or whether the starch granule as such gives protection. Since the starch granules of some plants are naturally of a suitable size, the granules need not necessarily be fractionated. Otherwise, the starch granules are fractionated into fractions of various size categories and a suitable starch granule fraction is chosen from the viewpoint of the purpose of use.

A suitable amount of starch granules, for example, 1 weight fraction is mixed with 10 to 100 weight fractions of a drug solution or another substance of a suitable concentration which is to be contained by the starch granules.

According to one preferred embodiment of the invention, the starch granules are filled with desired substances and freeze-dried.

According to another preferred embodiment of the invention, the starch granules are hydrolyzed, filled with desired substances, and freeze-dried after hydrolyzing and/or filling.

The hydrolyzed or unhydrolyzed starch granules are coated so that the substances encased within the starch granules cannot be released prematurely or that the environment cannot have an adverse effect on them. Coating is carried out after filling or after the freeze-drying subsequent to the filling.

After filling or after hydrolyzing and filling, the starch granules can be separated from the treating solution for various applications and freeze-dried, cooled down in a deep-freezer or in liquid nitrogen. As a result, a powder is obtained which is easy to treat and in which the capsules formed by the starch granules are separate.

The coating can be carried out by using a biopolymer which is capable of film forming, preferably a starch and most preferably an amylose. An 0.1–70% or 0.1–6% solution in proportion to the starch can be prepared from the starch or the amylose. The starch or amylose solution can be sprayed onto the surface of the granules so that the starch or amylose concentration is 1–6% of the weight of the granules, and allowed to cool so that the starch/amylose forms a gel on the surface of the granules. In this case, it is preferable to use an 0.1–6%, preferably an 0.1–2% starch solution. Alternatively, the granules can be mixed with the starch or amylose solution and allowed to crystallize at a low temperature (4–10° C.). In this case, it is preferable to use an 0.1–70% starch solution. The starch or amylose solution can also be precipitated on the granule surfaces by using ethanol. According to one alternative, the starch granules can be coated with starch particles of a smaller size than themselves, for example, of 1–10 $\mu$m.

The starch film coating can be implemented as a water-based coating which is a clear advantage compared with film coating using organic dissolvents (industrial safety, dissolvent residue, environmental aspects).

We could also consider combining the biopolymer, such as cellulose, pectin, protein or starch or amylose used for coating the capsule, with various film coating materials used in the pharmacy and accepted pharmaceutically. One protecting film material used in the pharmacy is, for example, hydroxy-propyl methyl cellulose (HPMC), regarding regulating film materials, we could mention ethyl cellulose which could be used to regulate the decomposition speed of the starch films in the alimentary tract. The coating material preferably consists of 50–100%, preferably 90–100% biopolymers, such as starch or amylose, the rest is 0–50%, preferably 0–10% pharmaceutically accepted film coating materials.

According to the invention, the granules can be filled with various substances, particularly with light-volatile ones, such as flavouring agents or polypeptides and proteins, particularly pharmaceutical peptides or proteins or drugs. Such drugs include, for example, caffeine, theophylline, propanolol hydrochloride, sodium indometacine, pentoxyphylline, verapamil hydrochloride, and pharamaceutical short-chained proteins and peptides.

The granules can be hydrolyzed either chemically or by using enzymes. The enzymes are preferably alpha-amylases, β-amylases and/or glucoamylases which typically originate from the Rhizopus, Aspergillus or Bacillus genera. Examples of suitable alpha-amylases and β-amylases include the enzymes of MEGAZYME® (Australia).

For hydrolysis, the starch granules are suspended in water to form about a 5–15% solution. The amount of the amylase solution added is 1000–10000 U/g of granules depending on the enzyme product. The hydrolysing is carried out at a temperature that is suitable for the activity of the enzyme but does not alter the structure of the starch, for example, at a temperature of 30–40° C. or, alternatively, under high pressure so that the temperature need not be so high. The objective of the hydrolysis is to hydrolyze 3–60%, preferably 30–50%, and most preferably 40% of the dry content of the chosen starch granules.

When drugs are covered by a capsule formed by a starch granule according to the invention, the efficacy of the drug after 6 months is still 50–70%, preferably 70–90% of the original efficacy of the drug.

The following non-limiting examples illustrate the invention.

EXAMPLE 1

1. Separation of Starch Granules

Potato starch is suspended in water (a 5% solution). The solution is poured into a glass tube (diameter 4 cm and height 15 cm). The solution is agitated and the granules are allowed to sediment for 8 minutes. Large granules (30–100 μm) sediment on the bottom of the tube. The solution (small granules) is poured from the top of the sediment to another container. The sedimentation is repeated 3 times. The sediment (large granules) is freeze-dried. The sediment is centrifuged and freeze-dried. The size distribution of the separated starch fraction (defined with Coulter) is presented in FIG. 1.

2. Hydrolysis of the Starch with Alpha-amylase

Starch granules are suspended in water (a 10% solution). An alpha-amylase solution (MEGAZYME®, Australia) with 1000–10000 U/g of granules is added. Hydrolysis is allowed to take place overnight at a temperature of over 30° C. in a water bath provided with a magnetic stirrer. The solution is centrifuged and the sediment is freeze-dried. About 3% of the dry content of potato starch and about 40% of the dry content of the large separated potato starch granules become hydrolyzed. A starch granule hydrolyzed with alphaamylase is presented in FIG. 2.

3. Use of Hydrolyzed Starch Granules

The starch granules are filled with propanolole hydrochloride in an aqueous solution at room temperature or at 40° C. at the most. The proportion of the starch and the drug is, for example, 1/1. The filled granules are freeze-dried.

4. Coating

For the coating, an amylose solution is prepared at 140–170° C. (0.1–70% of amylose in water). The solution is cooled down to room temperature and the granules are added to the solution. Ethanol is added to the solution so that the starch is precipitated. Thereafter, the solution is either dried at room temperature or freeze-dried after filtering. Instead of adding ethanol, the solution can be cooled at +5° C. for 6–12 hours, whereafter the solution is freeze-dried. FIG. 3 shows a starch granule coated with amylose.

What is claimed is:

1. A non-aggregated starch granule having a porous structure, said starch granule being filled with a desired substance and coated with a biopolymer or a mixture of a biopolymer and a pharmaceutically acceptable film coating material.

2. The starch granule according to claim 1, wherein said granule is filled with light-volatile compounds.

3. The starch granule according to claim 2, wherein said light-volatile compounds are selected from the group consisting of flavoring agents, spices, proteins and peptides.

4. The starch granule according to claim 1, wherein said granule is filled with one of the following drugs: caffeine, theophylline, propanolol hydrochloride, sodium indometacine, verapamil hydrochloride or pharmaceutical short-chained proteins or peptides.

5. The starch granule according to claim 1, wherein said granule is filled with an enzyme.

6. The starch granule according to claim 1, wherein said granule is coated with cellulose, pectin, protein, starch and/or amylose.

7. The starch granule according to claim 1, wherein said granule is coated with a mixture of cellulose, pectin, protein, starch and/or amylose and any pharmaceutically acceptable film coating material.

8. The starch granule according to claim 1, wherein, as a consequence of hydrolyzing, the structure of the starch granule is porous.

9. The starch granule according to claim 1, wherein said starch granule is hydrolyzed by using enzymes.

10. The starch granule according to claim 1, wherein said starch granule is hydrolyzed with alpha-amylase, β-amylase, and/or glucoamylase.

11. The starch granule according to claim 1, wherein said starch granule originates from barely, potato, wheat, oats, pea, corn, tapioca, sago, rice or similar tuber vegetable or grain crop.

12. The starch granule according to claim 1, wherein the size of the starch granule is 10–100 μm.

13. The starch granule according to claim 1, wherein said starch granule is coated with a starch solution having a concentration of 0.1–70% in proportion to the starch.

14. The starch granule according to claim 1, wherein said starch granule has a perforated surface that is filled with starch particles of a size of 1 to 10 μm.

15. A method for preparing starch granules, which method comprises the following steps:
   selecting non-aggregated starch granules of a suitable size in accordance with the purpose of use,
   filling the non-aggregated starch granules with a desired substance, and
   coating the starch granules with a biopolymer or a mixture of a biopolymer and a pharmaceutically acceptable film coating material.

16. The method according to claim 14, wherein the starch granules are coated by crystallizing or spraying a starch solution onto the surface of the granules.

17. The method according to claim 16, wherein the starch solution used for crystallizing is 0.1–70% in proportion to the starch.

18. The method according to claim 16, wherein the starch solution used for spraying is 0.1–6% in proportion to the starch.

19. The method according to claim 14, wherein said starch granules are coated by mixing the granules with an 0.1–70% starch solution which, when cooled, forms a gel on the surface of the granules.

20. The method according to claim 14, wherein said starch granules are coated by mixing the granules with a starch solution which, when precipitated by using ethanol, forms a gel on the surface of the granules.

21. The method according to claim 14, wherein said granules have a perforated surface that is filled with starch particles of a size of 1–10 μm.

22. The method according to claim 14, wherein said starch granules are hydrolyzed so that the structure of the granules becomes porous.

23. The method according to claim 14, wherein the starch granules are hydrolyzed by using enzymes.

24. The method according to claim 14, wherein said starch granules are hydrolyzed with alpha-amylase, β-amylase, and/or glucoamylase.

25. The method according to claim 14, wherein hydrolysis is allowed to take place so that 3–60% of the dry content of the starch granules is hydrolyzed.

26. The method according to claim 14, wherein said starch granules are hydrolyzed and filled simultaneously.

27. The method according to claim 14, wherein said starch granules are freeze-dried after hydrolyzing and/or after filling.

28. The starch granule according to claim 1, wherein said granule is filled with paramaceutical proteins or peptides or drugs.

29. The starch granule according to claim 11, wherein said starch granule originates from potato, barley, wheat or corn.

30. The starch granule according to claim 12, wherein the size of the starch granule is 50–100 μm.

31. The starch granule according to claim 13, wherein said starch granule is coated with a starch solution having a concentration of 0.1–6% in proportion to the starch.

32. The starch granule according to claim 31, wherein said starch granule is coated with a starch solution having a concentration of 0.1–2% in proportion to the starch.

33. The method according to claim 18, wherein the starch solution used for spraying is 0.1–2% in proportion to the starch.

34. The method according to claim 25, wherein hydrolysis is allowed to take place so that 30–50% of the dry content of the starch granules is hydrolyzed.

* * * * *